United States Patent [19]

Blay et al.

[11] Patent Number: 5,371,286
[45] Date of Patent: Dec. 6, 1994

[54] REMOVAL OF CARBONYL IMPURITIES FROM A CARBONYLATION PROCESS STREAM

[75] Inventors: George A. Blay; Madan Singh, both of Corpus Christi; Mark O. Scates, Friendswood; Wayne D. Picard, Houston, all of Tex.

[73] Assignee: Hoechst Celanese Corporation, Somerville, N.J.

[21] Appl. No.: 52,429

[22] Filed: Apr. 26, 1993

Related U.S. Application Data

[63] Continuation-in-part of Ser. No. 646,916, Jan. 1, 1991, Pat. No. 5,001,259.

[51] Int. Cl.$^5$ ............................................. C07C 51/12
[52] U.S. Cl. .................................................. 562/519
[58] Field of Search ........................................ 562/519

Primary Examiner—José G. Dees
Assistant Examiner—Joseph M. Conrad, III
Attorney, Agent, or Firm—Donald R. Cassady

[57] ABSTRACT

A method is provided to improve the quality of recycle of certain residues by modifying the separation of alkanes and alkane-like materials and carbonyl-containing impurities from the recycle during the manufacture of acetic acid by the carbonylation of methanol. The improvement comprises operating a prior art stripper column in a reflux manner and partitioning the residue therefrom by the addition of water. The method also reduces the volume of disposal of potentially valuable recyclable reactants.

4 Claims, 2 Drawing Sheets

REMOVAL OF CARBONYL IMPURITIES FROM A CARBONYLATION PROCESS STREAM

RELATIONSHIP TO PRIOR APPLICATION

This application is a continuation-in-part application of Ser. No. 07/646,916 filed on Jan. 1, 1991 now U.S. Pat. No. 5,001,259.

BACKGROUND OF THE INVENTION

This invention relates to a novel process for the purification of acetic acid which has been formed by the carbonylation of methanol or methyl acetate in the presence of a Group VIII metal carbonylation catalyst. More specifically, this invention relates to a novel process for removing alkane impurities from acetic acid formed by Group VIII metal catalyzed carbonylation processes.

Among currently-employed processes for synthesizing acetic acid one of the most useful commercially is the catalyzed carbonylation of methanol with carbon monoxide as taught in U.S. Pat. No. 3,769,329 issued to Paulik et al on Oct. 30, 1973. The carbonylation catalyst comprises rhodium, either dissolved or otherwise dispersed in a liquid reaction medium or else supported on an inert solid, along with a halogen-containing catalyst promoter as exemplified by methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. The patentees disclose a very large number of suitable promoters, most of which are organic iodides. Most typically and usefully, the reaction is conducted with the catalyst being dissolved in a liquid reaction medium through which carbon monoxide gas is continuously bubbled.

An improvement in the prior-art process for the carbonylation of an alcohol to produce the carboxylic acid having one carbon atom more than the alcohol in the presence of a rhodium catalyst is disclosed in copending, commonly assigned application U.S. Pat. No. 5,001,259, issued Mar. 19, 1991 and European patent application 161,874; published Nov. 21, 1985. As disclosed therein acetic acid is produced from methanol in a reaction medium comprising methyl acetate, methyl halide, especially methyl iodide, and rhodium present in a catalytically-effective concentration. The invention therein resides primarily in the discovery that catalyst stability and the productivity of the carbonylation reactor can be maintained at surprisingly high levels, even at very low water concentrations, i.e. 10 wt. % or less, in the reaction medium (despite the general industrial practice of maintaining approximately 14 wt. % or 15 wt. % water) by maintaining in the reaction medium, along with a catalytically-effective amount of rhodium, at least a finite concentration of water, methyl acetate, and methyl iodide, a specified concentration of iodide ions over and above the iodide content which is present as methyl iodide or other organic iodide. The iodide ion is present as a simple salt, with lithium iodide being preferred. The applications teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt. %, so low that it can broadly be defined simply as "a finite concentration" of water. Furthermore, the reaction medium employed improves the stability of the rhodium catalyst, i.e. resistance to catalyst precipitation, especially during the product-recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. Ser. No. 870,267 is herein incorporated by reference.

The acetic acid which is formed by the carbonylation of methanol is converted to a high purity product by conventional means such as by a series of distillations.

During the manufacture of acetic acid by the previously described methods one group of impurities found in the crude product is alkanes manufactured in the carbonylation process. This formation of alkanes was recognized by Price. His invention, described and claimed in U.S. Pat. No. 4,102,922, involved removing the alkanes by stripping the acidic products of the reaction away from the alkanes after removal of the catalyst. The reaction mixture is carried to a pressure let-down vessel denoted as a flasher where the products are vaporized and removed from a residue of catalyst. The catalyst is recycled to the reactor. The flashed product containing methyl iodide, water, acetic acid, and the alkanes is fed to a splitter and allowed to separate into at least two liquid phases, one phase containing acetic acid and water which is returned to the reactor and a second phase denoted herewithin as a heavy phase. To effect removal of the alkanes, a slipstream of the heavy phase from the splitter column is stripped using carbon monoxide as a stripping gas, removing the alkanes as the bottoms stream from the latter distillation.

We have discovered a method by which the alkanes can be removed according to the method of Price but with the unexpected benefit of realizing the recovery of acetic acid from the heavy phase that would normally be discarded by the practice of the prior art.

In a preferred embodiment of our invention we have found a method of effecting the alkanes removal at low-water conditions wherein the water balance in the reaction system is maintained.

SUMMARY OF THE INVENTION

The process of the present invention is directed to the a novel method for removing the alkanes from an acetic acid reaction resulting in the recovery of acetic acid and a more facile purification of acetic acid which has been formed by the carbonylation of methanol, dimethyl ether, methyl acetate, or a mixture thereof in the presence of a Group VIII metal carbonylation catalyst. Such carbonylation reactions comprise catalytic reaction with carbon monoxide in the presence of a halide promoter such as an organic halide as disclosed in U.S. Pat. No. 3,769,329 or under low water conditions such as disclosed in aforementioned U.S. Ser. No. 870,267 wherein the catalyst solution contains not only the Group VIII metal catalyst and organic halide promoter, but also contains an additional iodide salt. In such processes, a feed of methanol, dimethyl ether, methyl acetate, or mixture thereof is carbonylated in a liquid phase carbonylation reactor. Separation of products is achieved by directing the contents of the reactor to a flasher wherein the catalyst solution is withdrawn as a base stream and recycled to the reactor while the overhead which comprises largely the product acetic acid along with methyl iodide, methyl acetate, and water is directed to a methyl iodide-acetic acid splitter column. The overhead from the splitter column comprises mainly organic iodides and methyl acetate whereas from the base or side stream of the splitter column is drawn the acetic acid product which is usually directed to further purification by finishing distillation. It is a portion of this overhead, heavy phase, that contains a majority of the alkanes which are removed by the process of the present invention. In accordance with the process of the present invention, the heavy phase from the splitter column overhead is distilled in a refluxing column at a reflux ratio of from about 0.5 to about 5. The overhead from this refluxing column, containing methyl iodide, methyl acetate, and carbonyl impurities, is removed and can be returned to the reactor or can be further treated to remove the carbonyl impurities. The residue from this column is passed to a decanter where the phases are caused to separate by the addition of water. The bottom phase being substantially water and acetic acid is returned to the reactor. The upper phase being substantially all of the alkanes is waste and can be used as feed to an incinerator or the like for disposal. In a preferred embodiment of the invention the phases are caused to separate by the addition of a slipstream of the overhead from the acetic acid drying column further down in the purification train. By the use of this recycled drying column aqueous overhead the water balance in the reaction is maintained. This is extremely beneficial in reactions at high water content, i.e. 14–15 wt %, but is even more critical at low water concentrations.

DETAILED DESCRIPTION

Figure 1:
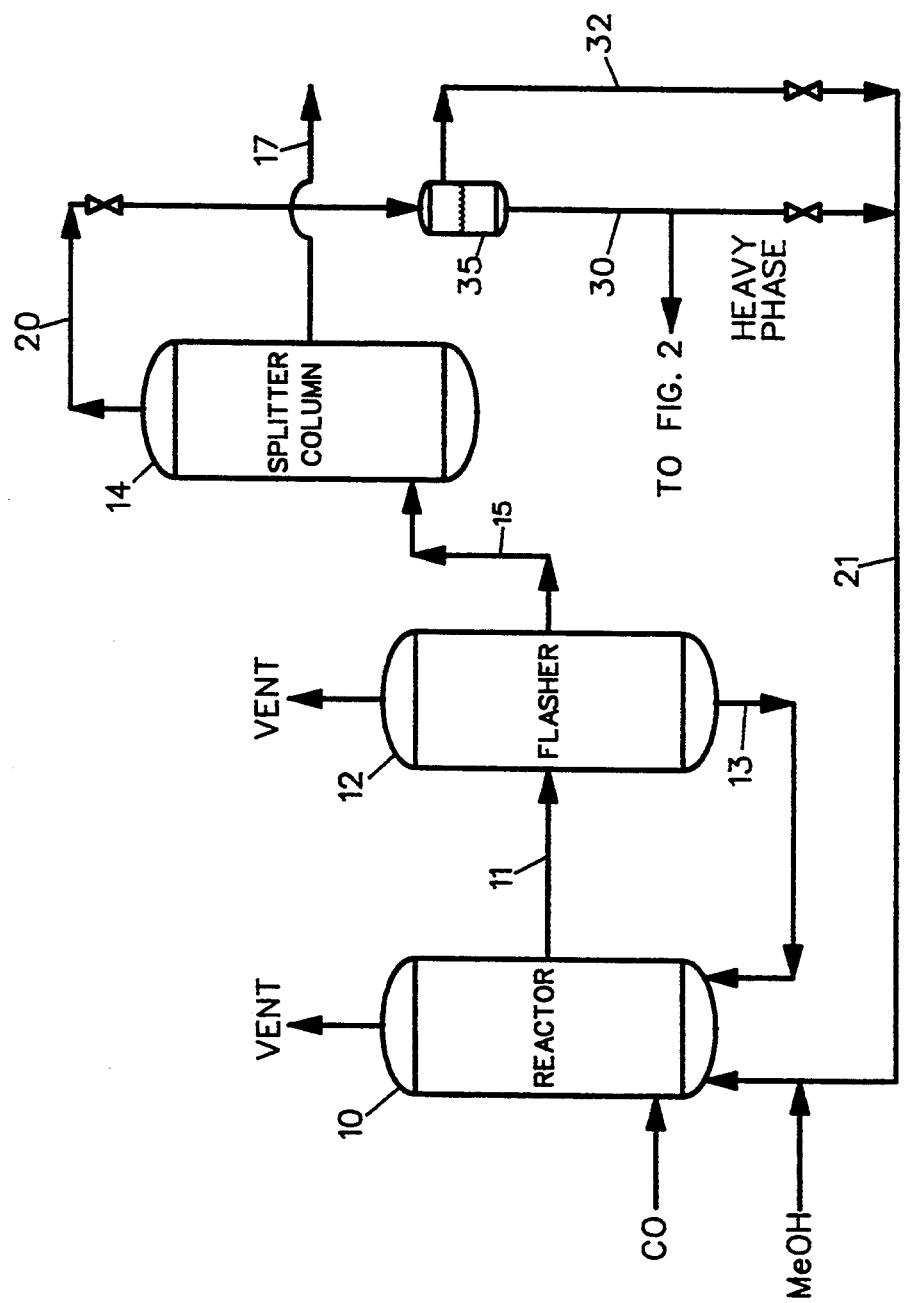

The purification process of the present invention is useful in any process used to carbonylate methanol, dimethyl ether, methyl acetate, and mixtures thereof to acetic acid in the presence of a Group VIII metal catalyst such as rhodium and an iodide promoter. A particularly useful process is the low-water rhodium catalyzed carbonylation of methanol to acetic acid as exemplified in aforementioned U.S. Ser. No. 870,267. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium. The rhodium component of the catalyst system may be provided by introducing rhodium into the reaction zone wherein the rhodium is in the form of rhodium metal, rhodium salts and oxides, organic rhodium compounds, coordination compounds of rhodium, and the like.

The halogen promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol which is carbonylated. Thus, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process comprises the caxboxylic acid product. Thus, in the carbonylation of methanol to acetic acid, the preferred solvent is acetic acid.

It is known that in rhodium-catalyzed carbonylation reactions of the type set forth in this invention, the addition of water exerts a beneficial effect upon the reaction rate (U.S. Pat. No. 3,769,329). Thus, commercial operations run at water concentrations of at least 14 wt. % (EP 055618). Accordingly, it is quite unexpected that reaction rates substantially equal to and above reaction rates obtained with such high levels of water concentration can be achieved with water concentrations below 14 wt. % and as low as 0.1 wt. %.

In accordance with the carbonylation process most useful to manufacture acetic acid, the desired reaction rates are obtained even at low water concentrations by including in the reaction medium methyl acetate and an additional iodide ion which is over and above the iodide which is present as a catalyst promoter such as methyl iodide or other organic iodide. The additional iodide promoter is an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously. This has not been recognized in the prior art previous to disclosure of commonly assigned U.S. Ser. No. 870,267. The concentration of lithium iodide used in the reaction medium of the preferred carbonylation reaction system is believed to be quite high as compared with what little prior art there is dealing with the use of halide salts in reaction systems of this sort.

The carbonylation reaction of methanol to acetic acid product may be carried out by intimately contacting the methanol feed, which is in the liquid phase, with gaseous carbon monoxide bubbled through a liquid reaction medium containing the rhodium catalyst, methyl iodide promoting component, methyl acetate, and additional soluble iodide salt promoter, at conditions of temperature and pressure suitable to form the carbonylation product. It will be generally recognized that it is the concentration of iodide ion in the catalyst system that is important and not the cation associated with the iodide, and that at a given molar concentration of iodide the nature of tile cation is not as significant as the effect of the iodide concentration. Any metal iodide salt, or any iodide salt of any organic cation, can be used provided that the salt is sufficiently soluble in the reaction medium to provide the desired level of the iodide. The iodide salt can be a quaternary salt of an organic cation or the iodide salt of an inorganic cation. Preferably it is an iodide salt of a member of the group consisting of the metals of Group la and Group IIa of the periodic table as set forth in the "Handbook of Chemistry and Physics" published by CRC Press, Cleveland, Ohio, 1975–76 (56th edition). In particular, alkali metal iodides are useful, with lithium iodide being preferred. In the low water carbonylation most useful in this invention, the additional iodide over and above the organic iodide promoter is present in the catalyst solution in mounts of from about 2 to about 20 wt. %, preferably 5–15 wt. %, the methyl acetate is present in mounts of from about 0.5 to about 30 wt. %, preferably 2–5 wt %, and the methyl iodide is present in amounts of from about 5 to about 20 wt. %, preferably 10–16 wt. %, and most preferably 12–15 wt. %. The rhodium catalyst is present in mounts of from 200–1000 and preferably 300–600 ppm.

Typical reaction temperatures for carbonylation will be approximately 150°–250° C., with the temperature range of about 180°–220° C. being the preferred range. The carbon monoxide partial pressure in the reactor can vary widely but is typically about 2–30 atmospheres, and preferably, about 3–10 atmospheres. Because of the partial pressure of by-products and the vapor pressure of the contained liquids, the total reactor pressure will range from about 15 to 40 atmospheres.

A typical reaction and acetic acid recovery system which may be used for the iodide-promoted rhodium catalyzed carbonylation of methanol to acetic acid is shown in FIG. 1 and comprises a liquid-phase carbonylation reactor 10, flasher 12, and a methyl iodide-acetic acid splitter column 14. The carbonylation reactor 10 is typically a stirred vessel within which the reacting liquid contents are maintained automatically at a constant level. Into this reactor there are continuously introduced fresh methanol, sufficient water as needed to maintain at least a finite concentration of water in the reaction medium, recycled catalyst solution from the flasher base, a recycled methyl iodide and methyl acetate phase, and an aqueous acetic acid phase from the overhead of the methyl iodide-acetic acid splitter column 14. Alternate distillation systems can be employed so long as they provide means for recovering the crude acetic acid and recycling catalyst solution, methyl iodide, and methyl acetate to the reactor. In the preferred process, carbon monoxide is continuously introduced into the carbonylation reactor 10 just below the agitator which is used to stir the contents. The gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. The temperature of the reactor is controlled automatically, and the carbon monoxide feed is introduced at a rate sufficient to maintain the desired total reactor pressure.

Liquid product is drawn off from carbonylation reactor 10 at a rate sufficient to maintain a constant level therein and is introduced to flasher 12 via line 11. In flasher 12 the catalyst solution is withdrawn as a base stream 13 (predominantly acetic acid containing the rhodium and the iodide salt along with lesser quantities of methyl acetate, methyl iodide, and water), while the overhead 15 of the flasher comprises largely the product acetic acid along with methyl iodide, methyl acetate, and water. Dissolved gases in stream 11 consisting of a portion of the carbon monoxide along with gaseous by-products such as methane, hydrogen, and carbon dioxide exits the top of the splitter column overhead receiver.

The product acetic acid drawn from the side of methyl iodide-acetic acid splitter column 14 near the base (it can also be withdrawn as a base stream) is directed via line 17 for final purification such as to remove water as desired by methods which are obvious to those skilled in the art including, most preferably, distillation. The overhead 20 from methyl iodide-acetic acid splitter, comprising mainly methyl iodide and methyl acetate plus some water and acetic acid, is recycled via line 21 to the carbonylation reactor 10. When overhead 20 is condensed it typically splits into two liquid phases in decanter 35 if sufficient water is present. The heavy phase 30 is comprised mainly of methyl iodide plus some methyl acetate and acetic acid as well as the alkane and carbonyl impurities. The light phase 32 is comprised mainly of water and acetic acid plus some methyl acetate. The overhead heavy phase 30 from methyl iodide-acetic acid splitter is subject to treatment according to this invention or these streams can be combined with recycle products from further purification processes containing methyl iodide, methyl acetate, water, and other impurities to become recycle 21 which may also be subject to treatment according to this invention.

In accordance with the carbonylation process of Price, loc cit, it has been found that the alkane impurities which accumulate in the overhead 21 are removed from this stream to prevent a substantial build-up of alkanes in the reactor thus providing an improvement in acetic acid product quality. According to Price, alkane removal is accomplished by the stripping of the material from stream 21 with a stream of carbon monoxide. The residue from this process separates into two phases upon cooling as we have shown in the Comparative Example shown below. The uppermost layer contains alkanes and alkyl iodides, while the lowermost layer contains predominately the acetic acid, propionic acid, and water. We have found that if the separation is carried out as a simple distillation in a reflux column wherein the reflux ratio is from about 0.5 to about 5, preferably from about 1 to about 3, and the bottoms from the column passed to a decanter the residue does not separate into two phases. If additional water is added then separation into the two phases occurs, and the separation proceeds with more of the alkanes partitioning into the upper layer and more of the acids partitioning into the aqueous lower layer than that shown by our comparison with the Price method. This enhanced separation provides a lowermost aqueous phase which contains additional recoverable acetic acid. This acetic acid can most advantageously be recycled to the reactor instead of being lost to the system according to the Price method.

In the preferred embodiment, the water for the separation is derived from an acetic acid drying column, a subsequent finishing column in the purification train. According to the preferred embodiment a slipstream from the overhead of the drying column containing predominately water, plus some acetic acid., methyl iodide, and methyl acetate is distilled to remove the light organic components such as methyl iodide and methyl acetate which are recycled to the reactor leaving the water and some of the acetic acid which is then used to enhance the separation of the bottoms from the reflux tower.

Figure 2:
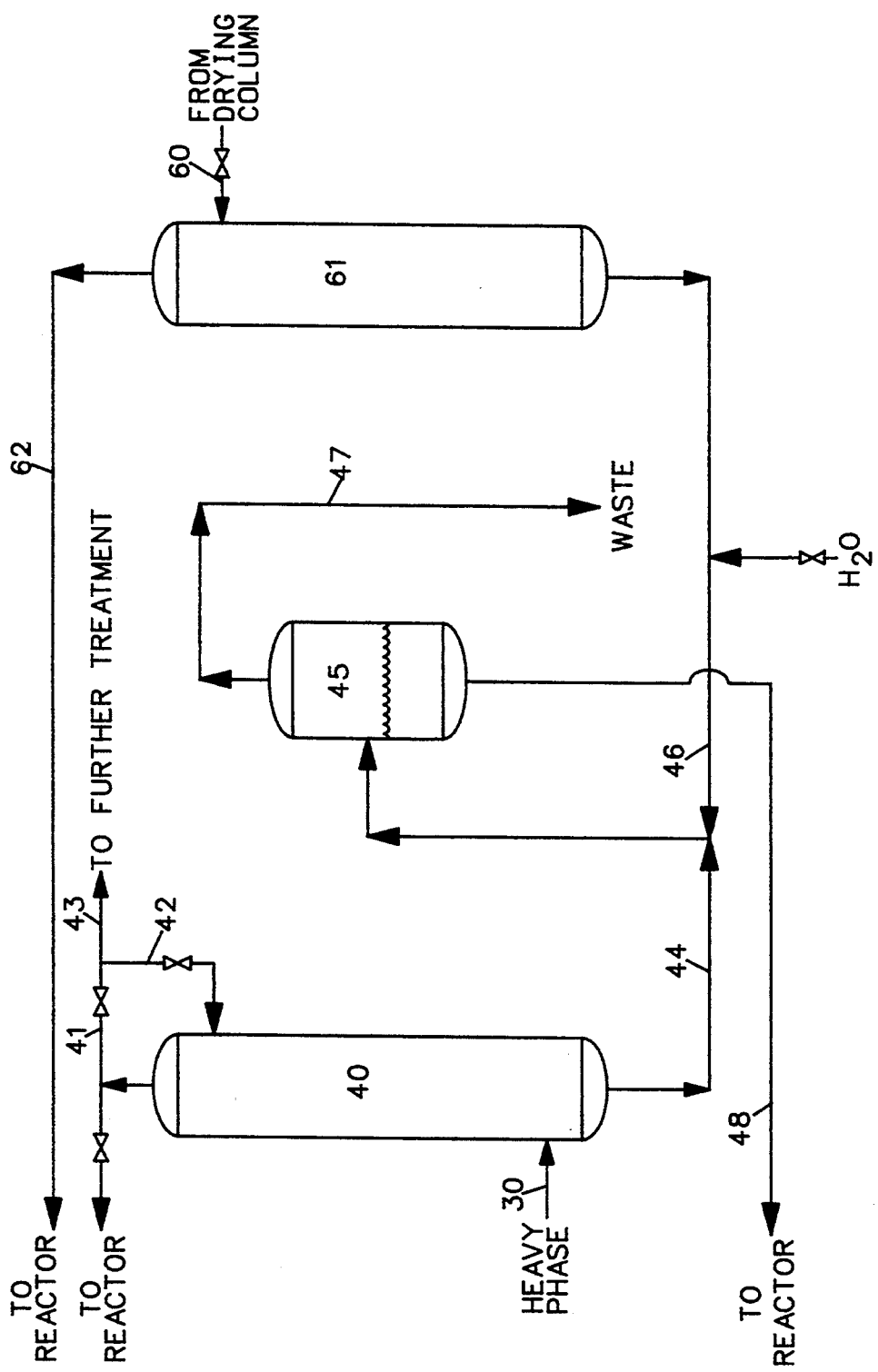

In the first stage of the present process as shown in FIG. 2, the heavy phase stream 30, which contains the alkane and carbonyl impurities, enters into reflux column 40 in which a reflux ratio of from about 1 to about 3 is maintained through streams 42 and 43. The overhead stream is either recycled to the reactor 10 or treated further to remove the carbonyl impurities, as for example according to the method of co-pending application Ser. No. 07/615,666 prior to being recycled to the reactor 10.

The residue from column 40, as stream 44, enters decanter 45. An aqueous stream 46 is also added to the decanter through stream 44 causing separation of the residue into two phases. The upper organic phase as stream 47 contains the alkanes which are disposed of in an environmentally sound manner and the lower aqueous phase as stream 48 contains the water and acetic acid which is recycled to the reactor 10.

In the preferred embodiment, stream 60, an aqueous slipstream from a drying column of the further purification train is distilled in column 61. The overhead from column 61 containing methyl iodide and methyl acetate is recycled to reactor 10 through stream 62. The aqueous residue is fed through stream 46 to the decanter 45 by combining the stream 46 with the stream 44, the residue from the reflux column 40, as an alternative to the addition of extraneous water. Alternatively, the stream 46 can be led directly into decanter 45 at a point in the side of the decanter most advantageous to cause effective separation of the phases in the decanter. The advantage of adding process water from the drying column into the decanter instead of extraneous water is to minimize the mount of water that must eventually be removed from the reaction system.

COMPARATIVE EXAMPLE 1

The residue from an alkane stripping column, operated in the manner of Price of an acetic acid manufacturing plant operating according to the method of Ser. No. 870,267, was allowed to separate into two phases. The phases were analyzed for composition which was expressed as weight per cent unless otherwise noted.

| Component | Upper | Lower | Combined Composition |
|---|---|---|---|
| Alkanes | 90.8 | 11.0 | 43.0 |
| Acetic Acid | 9.0 | 88.4 | 56.6 |
| Propionic Acid | 0.05 | 0.1 | 0.1 |
| Water | 0.05 | 0.3 | 0.2 |
| Other | 0.1 | 0.2 | 0.2 |
| Total Iodides | 1480 | 430 | 850 as ppm. |

EXAMPLE 1

A sample of the same material as above was mixed well with an equal volume of water and allowed to separate into layers. The layers were analyzed for composition which was expressed as weight per cent except as noted.

| Component | Upper | Lower | Combined Composition |
|---|---|---|---|
| Alkanes | 98.5 | 0.1 | 45.4 |
| Acetic Acid | 0.4 | 46.5 | 53.6 |
| Propionic Acid | 0.02 | 0.2 | 0.4 |
| Water | <0.5 | 53.0 | 0.3 |
| Others | 0.2 | 0.2 | 0.3 |
| Total Iodides | 2020 | <10 | 930 as ppm. |

COMPARATIVE EXAMPLE 2

OPERATION ACCORDING TO THE PRIOR ART

Samples were obtained from a commercial acetic acid plant operated in a manner described by Price in U.S. Pat. No. 4,102,922, the feed stream and residue from the stripping operation were analyzed. The results were as follows: (All numbers are as wt. % unless otherwise noted as ppm..)

| Component | Feed | Residue |
|---|---|---|
| Methyl iodide | 82.4 | 0.61 (as MeI + MeOAc) |
| Methyl acetate | 9.7 | |
| Acetaldehyde | 0.210 | 5.6 ppm. |
| Methanol | 0.170 | 54 ppm. |
| Butyraldehyde | 0.038 | 62 ppm. |
| Ethyl Iodide | 0.250 | 143 ppm. |
| 2-Ethyl Crotonaldehyde | <10 ppm. | 7.1 ppm. |

EXAMPLE 2

REFLUXING OPERATION OF COLUMN 40

A simulation of Column 40 was operated in the following manner using the same feed material as in Comparative Example 2:

Reflux ratio: 2
Overhead to feed ratio: 0.93
Pressure: 1 Atm.
Temperature: 102.3° C. at the bottom 41.4° C. at the top The feed, overhead, and residue were analyzed and the results were as follows.(all components were wt. % unless otherwise noted)

| Component | Feed | Overhead | Residue |
|---|---|---|---|
| Methyl iodide | 82.4 | 90.4 | <200 ppm. (as MeI + MeOAc) |
| Methyl acetate | 9.7 | 8.9 | — |
| Acetaldehyde | 0.210 | 0.195 | — |
| Methanol | 0.170 | 0.190 | — |
| Butyraldehyde | 0.038 | N.D. | — |
| Ethyl iodide | 0.250 | <100 ppm | 3.7 |
| Crotonaldehyde | 7 ppm | N.D. | — |
| Alkanes | 2.0 | 100 ppm | 21.2 |
| Water | 0.4 | 0.08 | 0.12 |
| 2-Ethyl Crotonaldehyde | <10 ppm | N.D. | — |

What is claimed is:

1. In a process for the carbonylation of one or more compounds of the group consisting of methanol, dimethyl ether, or methyl acetate to acetic acid wherein (1) said methanol, dimethyl ether, or methyl acetate is carbonylated in a reaction medium containing a Group VIII metal carbonylation catalyst and methyl iodide, (2) the products of said carbonylation separated into a volatile phase containing said acetic acid, unreacted dimethyl ether or methyl acetate, methyl iodide, alkane and carbonyl impurities, and a less volatile phase comprising said Group VIII metal catalyst, (3) said volatile phase distilled to yield acetic acid and an overhead containing unreacted methanol, dimethyl ether or methyl acetate, methyl iodide, alkane and carbonyl impurities and (4) further separating said overhead into a more volatile component and a less volatile component, the improvement which comprises:
    (a) conducting said separating by causing the volatile component to reflux in a refluxing column,
    (b) providing a reflux ratio of from about 0.5 to about 5 in the said reflux column,
    (c) removing the volatile portion for further processing,
    (d) separating the residue into two layers by the addition of water, and
    (e) recycling the aqueous layer to the reactor.
2. The process of claim 1 wherein the added water is obtained as water removed from a drying column of the acetic acid purification.
3. The process of claim 2 wherein the water from the drying column is further purified by stripping therefrom organic components prior to its being used as the added water.
4. The process of claim 1 wherein the reflux ratio is from about 1 to about 3.

* * * * *